(12) United States Patent
Kraft (10) Patent No.: US 8,426,814 B2
(45) Date of Patent: Apr. 23, 2013

(54) DETECTOR DEVICE

(75) Inventor: Gerhard Kraft, Darmstadt (DE)

(73) Assignee: GSI Helmholtzzentrum fuer Schwerionenforschung GmbH, Darmstadt (DE)

( * ) Notice: Subject to any disclaimer, the term of this patent is extended or adjusted under 35 U.S.C. 154(b) by 40 days.

(21) Appl. No.: 13/262,949

(22) PCT Filed: Apr. 6, 2010

(86) PCT No.: PCT/EP2010/002161
§ 371 (c)(1),
(2), (4) Date: Oct. 5, 2011

(87) PCT Pub. No.: WO2010/115608
PCT Pub. Date: Oct. 14, 2010

(65) Prior Publication Data
US 2012/0025076 A1    Feb. 2, 2012

(30) Foreign Application Priority Data

Apr. 7, 2009   (DE) .................. 10 2009 002 273

(51) Int. Cl.
*G01J 1/00*   (2006.01)

(52) U.S. Cl.
USPC ........................................ 250/336.1

(58) Field of Classification Search .... 250/336.1–336.2; 600/1; 378/108, 207
See application file for complete search history.

(56) References Cited

U.S. PATENT DOCUMENTS

| | | | |
|---|---|---|---|
| 3,838,284 A | 9/1974 | McIntyre | |
| 5,704,890 A * | 1/1998 | Bliss et al. | 600/1 |
| 6,087,664 A * | 7/2000 | Gripp et al. | 250/394 |
| 2007/0181815 A1* | 8/2007 | Ebstein | 250/370.11 |
| 2007/0252093 A1* | 11/2007 | Fujimaki et al. | 250/492.3 |
| 2010/0006769 A1 | 1/2010 | Kraft et al. | |
| 2011/0186720 A1* | 8/2011 | Jongen et al. | 250/252.1 |

FOREIGN PATENT DOCUMENTS

WO    WO 2008009528 A1    1/2008

OTHER PUBLICATIONS

Kang, Byung-Hwi; Jong-Won Kim, *Monte Carlo Design Study of a Gamma Detector System to Locate Distal Dose Falloff in Proton Therapy*, IEEE Transactions on Nuclear Science, New York, NY, US, vol. 56, No. 1, pp. 46-50, Feb. 2009.

Min, Chul Hee; Park J G; Kim C H, *Development of an Array-Type Prompt Gamma Detection System for the Online Measurement of the Range of the Proton Beam in a Patient: a Monte Carlo Feasibility Study* Journal of the Korean Physical Society, vol. 52, No. 3, pp. 888-891, Mar. 2008.

Testa E; Bajard M; Chevallier M; Dauvergne D; Le Foulher F; Freud N; Letang J M; Poizat J C; Ray C; Testa M, *Dose profile monitoring with carbon ions by means of prompt-gamma measurements*, Nuclear Instruments & Methods in Physics Research, Section—B:Beam Interactions With Materials and Atoms, Mar. 1, 2009 Elsevier, Amsterdam, NL, vol. 267, No. 6, pp. 993-996.

European Patent Office, International Search Report in International Patent Application No. PCT/EP2010/002161 (Jun. 27, 2011).

\* cited by examiner

*Primary Examiner* — Kiho Kim
(74) *Attorney, Agent, or Firm* — Leydig, Voit & Mayer, Ltd.

(57) ABSTRACT

A detector device detects the penetration depth of a particle beam applied to a target volume. The detector device includes a first detection device and a second detection device. The second detection device is configured to detect photons that are formed in the target volume and is disposed behind the first detection device with respect to a direction of the particle beam.

20 Claims, 7 Drawing Sheets

Parallel incidence:

Fig. 3 a

Oblique incidence:

DETECTOR DEVICE

CROSS REFERENCE TO RELATED APPLICATIONS

This application is a U.S. National Phase application under 35 U.S.C. §371 of International Application No. PCT/EP2010/002161, filed on Apr. 6, 2010, and claims benefit to German Patent Application No. DE 10 2009 002 273.2, filed on Apr. 7, 2009. The International Application was published in German on Oct. 14, 2010 as WO 2010/115608 A2 under PCT Article 21 (2).

FIELD

The present invention relates to a detector device, to a radiation device and to a method for determining the penetration depth of a particle beam applied to a target volume.

BACKGROUND

The irradiation of a target volume in an irradiation volume of an object with ion beams or particle beams relates to the irradiation of matter, especially organic, inorganic and biological materials, and it is used in various fields of research, industry and medical technology. In this context, the target volume comprises particularly the region in which a prescribed dose is to be deposited in order to modify the irradiated material; in particular, the irradiation volume also encompasses those regions of the material that are penetrated by the radiation, whereby the desired dose is then applied to the target volume. The term "particle beam" or "ion beam" refers especially to a high-energy beam consisting either of charged particles such as, for example, protons, carbon ions or ions of other elements, pions or else of neutral particles such as, for instance, neutrons. In the description below, the terms "ion beam" and "particle beam" are used synonymously. High energy refers especially to the energy of the particles in the range from several MeV/amu to several GeV/amu (amu: atomic mass unit).

A radiation device that is suitable for performing the irradiation generally has an acceleration means that generates and shapes the ion beam, and, for purposes of the irradiation, said ion beam is conducted by means of a beam transport system into a region in which the irradiation volume is situated. Furthermore, the radiation device comprises a beam modification means that can adapt the parameters of the ion beam to the position and size of the target volume. In particular, the beam modification means is also referred to as an application system that specifies the energy, direction and fluence or dose of the ion beam in such a way that the dose distribution corresponds approximately to the position and size of the target volume.

The irradiation volume can be simulated, for example, by a detecting means that serves to verify an irradiation field. The irradiation volume generally comprises an irradiation field that is a field with a maximum extension in the lateral direction, in general in the x- and y-directions, and that lies perpendicular to the direction of the ion beam. Here, the detecting means can consist of a verification field or of a so-called stack with several laterally extended verification fields arranged one behind the other. In the realm of dosimetry, for example, films with a photographic emulsion are used. Moreover, core trace detectors are employed for measuring the fluence distribution in the irradiation field. In the realm of medical applications, the irradiation of biological tissue is used in order to study the effect of particle irradiation so as to be able to estimate the effect of exposure to cosmic radiation in outer space.

Finally, the target volume in the irradiation volume can also be the volume of a tumor in a patient. As a rule, the irradiation volume here is specified by the attending physician and it comprises the actual target volume, that is to say, the tumor volume, as well as a safety margin around the visible tumor volume. Ion beams are used here to destroy the tumor tissue within the irradiation volume.

In tumor therapy, the special properties of ion beams make it possible to expose the tumor tissue to a very high dose, yet with minimal damage to the surrounding healthy tissue. This is mainly due to the favorable depth-dose distribution of ion beams. When high-energy ion beams penetrate into the material, they initially deposit little energy. As the depth increases, the specific energy deposition rises, reaches its maximum in the area of a distribution curve referred to as a Bragg peak, and then drops sharply. As a result, even with deeper tumors, more energy can be deposited in the tumor tissue than in the surrounding healthy tissue. Moreover, for heavy ions such as, for example, carbon ions, the biological efficacy increases in the maximum of the Bragg peak.

The target volume is generally scanned one slice or one layer at a time in the direction of the particle beam (z-direction) in that the Bragg peak is shifted or scanned in the z-direction over the target volume. As a rule, this shift of the Bragg peak is carried out in that the energy of the particle beam is changed. In this process, the target volume is divided into so-called iso-energy layers, and the various iso-energy layers each have a differing energy of the particle beam. The lateral scanning of the target volume is generally carried out in that the particle beam scans an iso-energy layer in the x-, y-plane, preferably one dot at a time. The x-y plane is essentially perpendicular to the iso-energy layer in question. A scanning dot is generally referred to as a matrix dot, so that the target volume is divided into matrix dots, each with x-, y-, z-coordinate points that are preferably scanned consecutively and to which a specific dose of the particle beam is applied.

In this process, the body to be irradiated (especially a volume region inside the body that is to be irradiated) can be static/unmoving or moving. It can happen that the irradiation volume in the irradiated object or in parts thereof, especially the target volume that is to be irradiated, is moving. A movement can be made not only translatorily relative to an external coordinate system, but rather also in the form of a shift of various regions of the body that is to be irradiated relative to each other (including twisting and deformations).

In order to be able to irradiate intrinsically moving bodies, so-called four-dimensional irradiation methods are used. In actual fact, these are three-dimensional irradiation methods that have a time variation (with time as the fourth dimension). Examples of such material processing methods can be found in the realm of material sciences in the production of highly integrated components (especially microprocessors and memory chips) as well as in the production of microstructured and nanostructured mechanisms.

Scanning methods can be used. In particular, three specific approaches are discussed. These are so-called rescanning methods, gating methods and tracking methods.

In the case of rescanning methods, the body that is to be irradiated undergoes a large number of consecutive irradiation procedures. On the statistical average, a sufficiently strong irradiation of the target volume is achieved if the moving body (or the target region that is to be irradiated) has a cyclically recurring movement pattern. However, it is problematic that this almost unavoidably results in a relatively high radiation dosage of the partial regions of the target body that should, in fact, not be irradiated. Moreover, the principle of rescanning processes means that they lend themselves primarily for relatively fast, cyclically recurring movements.

In the case of gating methods, an active irradiation of the target body only takes place when the volume region that is to be irradiated is located in a relatively narrowly delimited, defined region. At other points of time, however, no irradiation occurs (as a rule, because the particle beam is switched off). Fundamentally, gating methods yield good irradiation results. A drawback, however, is the longer irradiation duration that, among other things, entails higher costs.

An especially promising approach is offered by the tracking methods. Here, the region that is exposed to the irradiation is tracked, corresponding to the movement of the volume region of the target body that is to be irradiated. Tracking methods combine the advantages of a precise, targeted treatment with relatively short irradiation times.

The success of tumor therapy based on irradiation of the target volume, and thus of the tumor, depends largely on the extent to which the effective part of the ion beam can be concentrated exclusively onto the target volume.

For this reason, it is desirable to know, as precisely as possible, the exact position of the ion beam in the target volume of an object during its irradiation.

A laminated gamma detector is shown in FIGS. 1 and 2 as well as on page 19, line 21 through page 21, line 14 of WO 2008/009528, which is incorporated by reference herein in its entirety. This reference describes a detection system in conjunction with searching for land mines that is direction-sensitive. Further, WO 2008/009528 describes, especially on page 23, line 28 through page 27, line 32, pertaining to FIGS. 3, 4 and 5, that electrons that strike obliquely will have less of a chance to deposit their energy into one plate.

SUMMARY

In an embodiment, the present invention provides a detector device detects a penetration depth of a particle beam applied to a target volume. The detector device includes a first detection device and a second detection device. The second detection device is configured to detect photons that are formed in the target volume and is disposed behind the first detection device with respect to a direction of the particle beam.

BRIEF DESCRIPTION OF THE DRAWINGS

Embodiments of the present invention are described in more detail below with reference to the accompanying drawing. The same or similar objects are designated with the same reference numerals. In the drawings.

DETAILED DESCRIPTION

In an embodiment, the present invention provides a method and a detector device for determining the position of a particle beam applied to a target volume. In another embodiment, the present invention provides a radiation device having such a detector device.

A detector device according to an embodiment of the invention for detecting the penetration depth of a particle beam applied to a target volume has at least one detection means that is equipped and configured to detect the photons, especially gamma quanta, that are formed in the target volume. In this manner, it is possible to detect the prompt gamma rays that are formed in the target volume during the deceleration of the particles, especially ions. The prompt gamma rays are photons with an energy distribution of several MeV and they preferably have a continuous energy distribution between approximately 3 MeV and 10 MeV. The prompt gamma rays are emitted essentially isotropically around the target volume. Thus, the at least one detection means can be arranged in any angular direction, especially radially around the target volume. Preferably, the detection means is arranged laterally and/or below or behind the target volume, as seen in the direction of the ion beam. The gamma rays can advantageously be measured at the point in time when the target volume is irradiated with the particle beam, since the gamma rays are formed in the target volume due to the deceleration process of the ions. Consequently, the photons can be detected simultaneously with the irradiation at which the particle beam can be applied to one or more matrix dots of the target volume. In other words, the photons are measured at the point in time when the particle beam is applied to the target volume. The information obtained can advantageously be used during the further execution of the irradiation and especially in order to control the further course of the irradiation. In this process, for example, an energy correction of the particle beam can be undertaken, since the penetration depth was determined. Moreover, for example, if a tracking method is used, the energy of the particle beam can be tracked with the information obtained from the detection means. If this is an irradiation process using rescanning, then the information about the penetration depth obtained with the detection means can be used to carry out the further course of the irradiation, especially the rescanning parameters.

In a preferred embodiment of the detector device, an additional detection means is provided, wherein the additional detection means is a first detection means and the at least one detection means is a second detection means, wherein the second detection means is arranged behind the first detection means as seen in the direction of the particle beam. As a result, through the arrangement of the first detection means and second detection means relative to each other, it is possible to measure especially a spatial distribution of the particle beam and/or its dose deposition in the target volume. An especially three-dimensional direction-resolved detection of the especially high-energy photons or prompt gamma quanta that are formed by the irradiation of the target volume with the particle beam can be achieved. Preferably, the first detection means is provided for measuring a first quantity that characterizes the particle beam, and the second detection means is provided for measuring a second quantity that characterizes the particle beam. In this process, the photons can preferably be counted in the second detection means and thus, the fluence of the particles in the ion beam can be determined. However, the photons can also be measured by analog means.

Preferably, the first detection means can measure the direction of the particle beam while the second detection means can measure the intensity of photons being formed in the target volume. Here, the first detection means can preferably be arranged in such a way that it is irradiated or penetrated by the particle beam before it strikes the target volume and is preferably decelerated there and thus deposited. As a result, a distribution of the particle beam, in particular a location as seen in the x- and/or y-direction relative to the target volume, can be determined especially on the basis of the measurement of the first detection means. The second detection means can determine the location in the target volume in the z-direction and thus the penetration depth of the ion beam. Since the second detection means preferably detects the photons that strike it, it can be determined in which iso-energy layer of the target volume a specific dose was deposited. This can be done in that the number of gamma rays being formed is determined, especially counted. On this basis, the dose of the particles that have already been deposited in the target volume can be determined, for instance, through integration of the counted particles. Preferably, the measurement with the first detection means and the measurement with the second detection means can be carried out simultaneously. In particular, the dose can be measured essentially at the point in time when the photons are formed.

Here, it is advantageous that, by means of the detector device described above, a local distribution of the particle beam and its dose deposition in a target volume of an object, especially a patient, can be measured non-invasively and, above all, simultaneously. The dose distribution determined during the irradiation—application of the particle beam—can be used to control the irradiation, especially the application. This can be important particularly for an active application of irradiation, for example, a rescanning and/or tracking method, in which, among other things, successive individual small partial volumes of the target volume are irradiated.

In a preferred embodiment of the detector device, the first detection means is equipped and configured in such a way that the first detection means can determine the direction of the particle beam in at least one lateral dimension. The first detection means can be a first detector that is preferably a transmission detector and that leaves the particle beam essentially unchanged. The first detection means can especially be a spatially resolving detector; for example, the first detection means can be a wire chamber or a pixel ionization chamber. Preferably, the first detection means is a detector with a low area density.

In a preferred embodiment, the first detection means of the detector device is equipped and configured in such a way that the first detection means can determine the direction of the particle beam in at least a second lateral dimension that differs from the first. In this manner, the x- and/or y-coordinates are specified for the particle beam that strikes a specific target irradiation point in the target volume, which is referred to as a matrix dot or voxel. Therefore, the location or the position of the particle beam in the target volume can essentially be determined by determining the direction of the particle beam. Particularly in combination with parameters of the beam control, the direction of the particle beam in the target volume can be determined on the basis of the determination of the lateral (x-, y-) position in the first detection means. The position of the particle beam in the target volume can, at the same time, be the location where the high-energy photons are formed.

The second detection means of the detector device is preferably equipped and configured to determine the penetration depth of the particle beam in the target volume by means of the spatially resolved measurement of photons being formed in the target volume, preferably high-energy photons in the energy range below and up to several MeV. Since the target position of the particle beam in the target volume, especially in the Bragg peak, is the location where high-energy photons are formed, the determination of the location where the photons are formed makes it possible to measure the position of the Bragg peak of the particle beam applied to the target volume as well as the penetration depth of the particle beam in the target volume. In this process, the location where the photons are formed can be determined by the second detection means, especially in that the photons are detected outside of the target volume in a spatially resolved manner. The spatial distribution of the photons exiting the target volume is preferably isotropic. Preferably, the second detection means is arranged laterally with respect to the target volume and outside of the axis of the particle beam. Especially preferably, the second detection means is preferably arranged radially around the axis of the particle beam, especially on an axis that is oriented radially from the target volume towards the outside.

Here, at last one gamma detector that performs spatially resolved measurements can be used as the second detection means. Preferably, the second detection means of the detector device has a lamellar structure. The lamellae of the second detection means are preferably arranged so that one face of said lamellae is oriented perpendicular to the axis of the particle beam. Here, the second detection means can also be made up of plates, and said plates can be arranged parallel to each other. The plates form a so-called plate stack. The narrow sides of the plates can be oriented in the direction of the target volume. The extension of the plate stack in the direction of the beam axis is preferably equal to or larger than that of the target volume. Preferably, the face of the plate stack is arranged essentially parallel to the beam axis. Here, the faces of the individual plates can be oriented parallel to the beam direction. Consequently, the photons from the target volume can strike the face of the individual plates. Depending on the location in the target volume, the photons strike different plates at a different angle. The photons emit their energy into one plate or into several plates, or else they deposit their energy into the plate through which they pass. Here, electrons are formed by various processes such as Compton scattering, photoelectric effect and pair production. Since the plates or lamellae are preferably thin, this allows an adequate separation of different sites of origin of the photons in the target volume and thus a good spatial resolution. Due to the momentum conservation law, the electrons being formed in the individual plates are scattered forward. Consequently, they are scattered in the direction of the propagation of the originally formed photons. Thus, only the electrons that strike a detector plate or detector lamella perpendicularly can deposit all of their energy into it. Electrons that strike obliquely will have less of a chance to deposit all of their energy into one plate, but rather, the energy will be measured in two or more plates. The energy measured per plate will be lower for such electrons than for electrons that have emitted their energy into one plate. Hence, on the basis of the emitted energy that is measured in each plate, the direction of the photons and thus the site of origin in the target volume can be determined. Therefore, the photons, especially gamma quanta, that are formed in the target volume can be detected in a spatially resolved manner.

The preferred detector device is characterized in that the second detection means is designed as a stop detector, and the second detection means is preferably arranged behind the target volume, as seen in the beam direction. Preferably, the second detection means is arranged on the beam axis or at least symmetrically to the beam axis. All generally known plastic detectors can be used as stop detectors. It is also conceivable to use diamond detectors, especially polycrystalline diamond detectors. The stop detectors are preferably arranged at the distal end of the target volume, especially behind the target volume as seen in the direction of the particle beam. In particular, the stop detectors have a fixed position. The site of origin, especially in the z-direction, of the photons, especially prompt gamma rays, can be determined on the basis of the position, that is to say, the distance from the target volume to the second detection means, and on the basis of the measured time-of-flight. A laser pulse that initiates the generation of the particle beam can serve as the starting signal for the time-of-flight measurement. On this basis, in turn, the position of the particle beam in the individual matrix dot or voxel can be determined. Additional stop detectors can also be provided. In particular, the additional stop detectors can be arranged at different angles relative to the axis of the particle beam. On this basis, the position of partial beams being formed in the target volume can be reconstructed by means of computational algorithms.

The present invention also provides a radiation device for irradiating a target volume in an object that has at least one acceleration means, that has a beam generation means and a beam forming means as well as a control means for controlling the particle beam, and at least one detector device according to an embodiment of the invention. The acceleration means can be a generally known accelerator such as a synchrotron or a cyclotron with which particle beams in the range from a few hundred MeV to a few tens of GeV can be generated. The acceleration means, however, can also preferably be a laser-induced accelerator. It is advantageous here that the laser beam can function as a starting signal for a detector device with a second detection means that is used as a stop detector. In the case of a laser-induced accelerator, a laser beam with a very high output (petawatt laser) is fired onto a film. Among other things, this gives rise to charged particles from which a particle beam can be formed. This can then be fired at a target volume and deposited there, a process in which the particles are also deposited in a Bragg peak and prompt gamma rays are formed due to the deceleration.

In a preferred embodiment of the radiation device, the detector device is equipped and configured in such a way that it generates a control signal that can be fed to the control means of the radiation device. The control means can control the irradiation, especially online, preferably simultaneously with the irradiation. In particular, regarding the penetration depth of the particle beam, the control signal from the detector device can be used to scan or track successive matrix dots of the target volume.

Preferably, the radiation device is characterized in that the detector device has at least one detection means to detect photons, especially high-energy gamma rays. Preferably, a first detection means and/or at least one second detection means are provided, wherein the first detection means and the at least one second detection means are arranged in at least two different positions relative to the target volume, preferably in two positions that are perpendicular to each other. Preferably, at least the second detection means is arranged to the side of the target volume. In particular, the second detection means can be arranged at a position radially around the target volume. Here, said second detection means can be arranged geodetically in the plane of the target volume or below the target volume.

The present invention also provides a method for determining the penetration depth of a particle beam into an object, especially into a target volume of the object, wherein photons, especially gamma quanta, that are formed in the object by an interaction of the particle beam are detected by means of at least one detector device, especially a detector device according to an embodiment of the invention.

Preferably, the direction of the particle beam, especially the lateral location of the particle beam in the target volume, can be detected, especially with a spatially resolved detection means. In this process, the detection means can determine the location of the particle beam in the target volume as the site of origin of at least one photon. This can be done on the basis of a measurement of the energy of the photon or of the electron formed from it, which is measured in the detection means.

Preferably, with this method, the photons, especially gamma quanta, can be detected independently of each other at several positions outside of the axis of the particle beam. Consequently, a lamellar detection means with thin lamellae can be used.

Preferably, the method is configured in such a way that the site of origin of the photons in the target volume of the object that is irradiated with the particle beam is determined by measuring the time-of-flight of the photons from the site of origin in the target volume to a detection means. The detection means here is preferably a gamma detector. The time-of-flight measurement here is preferably started by a signal from the laser that generates the particle beam.

Consequently, the method is suitable for determining the location of a particle beam that is applied to a target volume, wherein the location of photons being formed in the target volume is detected. Here, in particular, the penetration depth of a particle beam into a body can be determined, and especially the time-of-flight of gamma quanta that are formed in the target volume by an interaction of the particle beam can be detected.

The special technical features and advantages of the devices described above and of the method are described and discussed together. Here, the features and advantages of the devices can be applied to the method and are valid for it, and vice versa.

Figure 1:
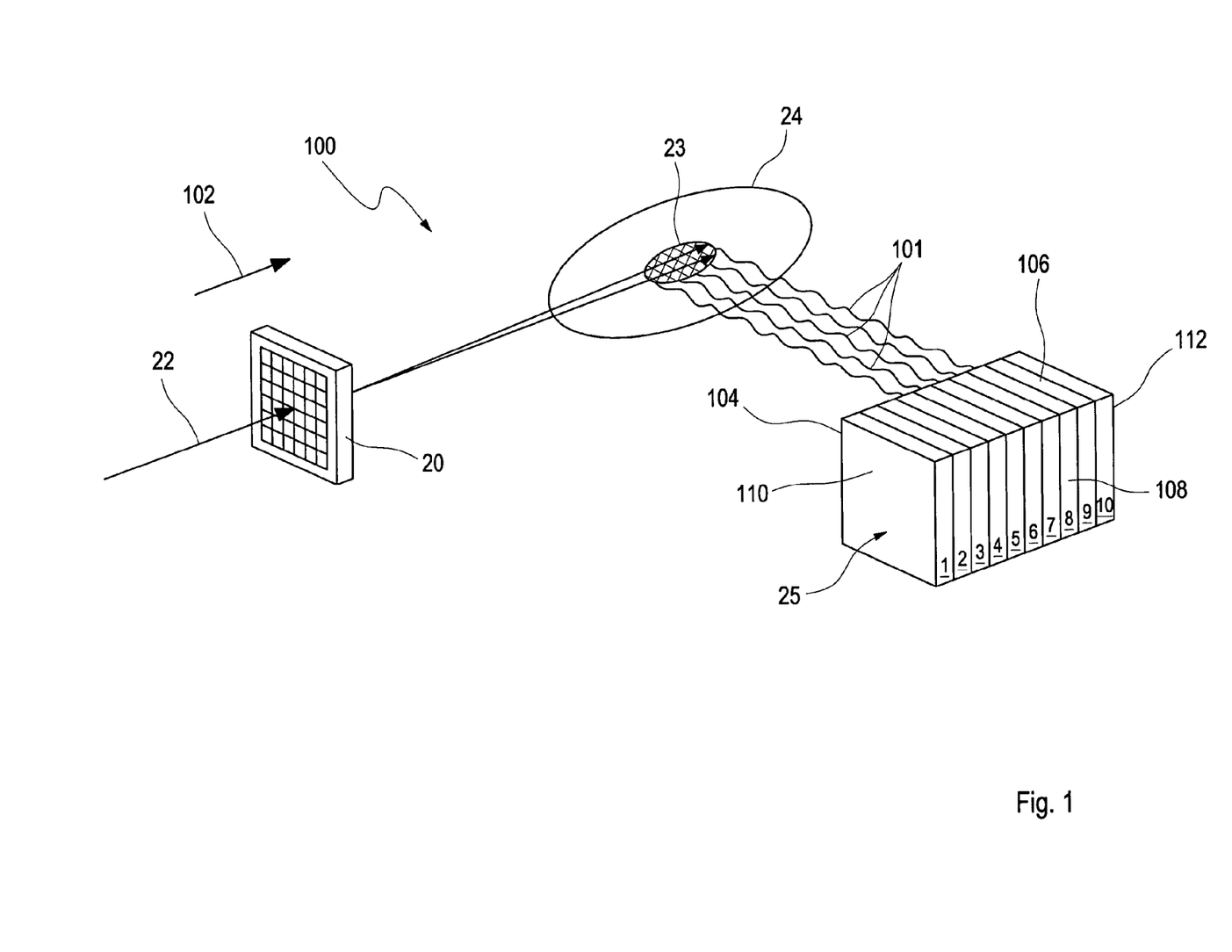
FIG. 1 shows a detector device with a first detection means and a second detection means.

FIG. 1 shows a schematic view of a detector device 100 with a first detection means 20 and a second detection means 25. The first detection means 20 is arranged in front of the second detection means 25 as seen in the beam direction 102, which shows the direction of a particle beam 22 and is indicated by the arrow 102. Here, the particle beam 22 can be an ion beam, especially a beam of protons, helium ions, carbon ions, neon ions or oxygen ions. The beam 22 can also have pions or muons as well as mixtures of two or more of the above-mentioned particles.

The ion beam 22 can be generated either in an acceleration means with an ion source (not shown here), or in an acceleration means driven by a laser beam. In this context, the generation of the particle beam 22 is inconsequential for the mode of operation of the detector device 100. The energy of the particle beam 22 is typically several tens of MeV/amu to several GeV/amu. Here, the energy of the particle beam 22 is selected in such a way that the particle beam 22 is suitable for the irradiation of a target volume 23 in an object 24, for example, a patient 24. The object 24, especially the patient 24, is drawn here schematically as an ellipse 24. However, the object 24 can also be a phantom and can serve for the verification of irradiation parameters before and after the irradiation of a patient. Here, the energy is typically selected in such a way that the particle beam 22 penetrates a few centimeters into the object 24 and is stopped in the target volume 23. The energy loss of the particle beam 22 here typically corresponds to a Bragg distribution. In the target volume 23, photons are formed that are indicated by wavy arrows 101. The energy distribution of the photons being formed is explained in greater detail in conjunction with FIG. 6. The photons are emitted from the target volume 23 and can be detected outside of the target volume 23. The angular distribution of the exiting photons is typically isotropic. Photons can be detected in one or more detection means that are arranged radially around the beam axis. The photons being formed are also referred to as prompt gamma quanta.

The second detection means 25 is structured as a laminar detector and has plates or lamellae 1, 2, 3, 4, 5, 6, 7, 8, 9 and 10. The number of plates 1 to 10 or lamellae 1 to 10 is to be understood merely by way of an example and not in any limiting sense. The mode of operation of the detection means 25 is explained in greater detail in the description pertaining to FIGS. 2 and 3. The second detection means 25 is shown in an oblique view. The second detection means 25 has a face 104 that is facing the target volume 23. Moreover, said second detection means 25 has a back 108 on the back, facing away from the target volume 23, as well as a first side 110 and a second side 112 as well as a top 106.

The first detection means 20 is preferably a spatially resolving detector or a detector that performs spatially resolved measurements and that can detect where the particle beam 22 passes through said detector. An area density of the detection means 20 is selected here in such a way that the detection means 20 is a transmission detector. Preferably, the first detection means 20 is an ionization chamber, a wire chamber or a pixel ionization chamber. The first detection means 20 can especially be a pixel ionization chamber with a resolution of 1812×1707 pixels. However, pixel ionization chambers with smaller pixel values can also be used. Typically, a resolution of less than 3 mm can be achieved. Typically the resolution is in the μm range, especially smaller than or approximately equal to 100 μm. Typical geometric dimensions of the first detection means 20 can be approximately 40 cm×40 cm.

Figure 2:
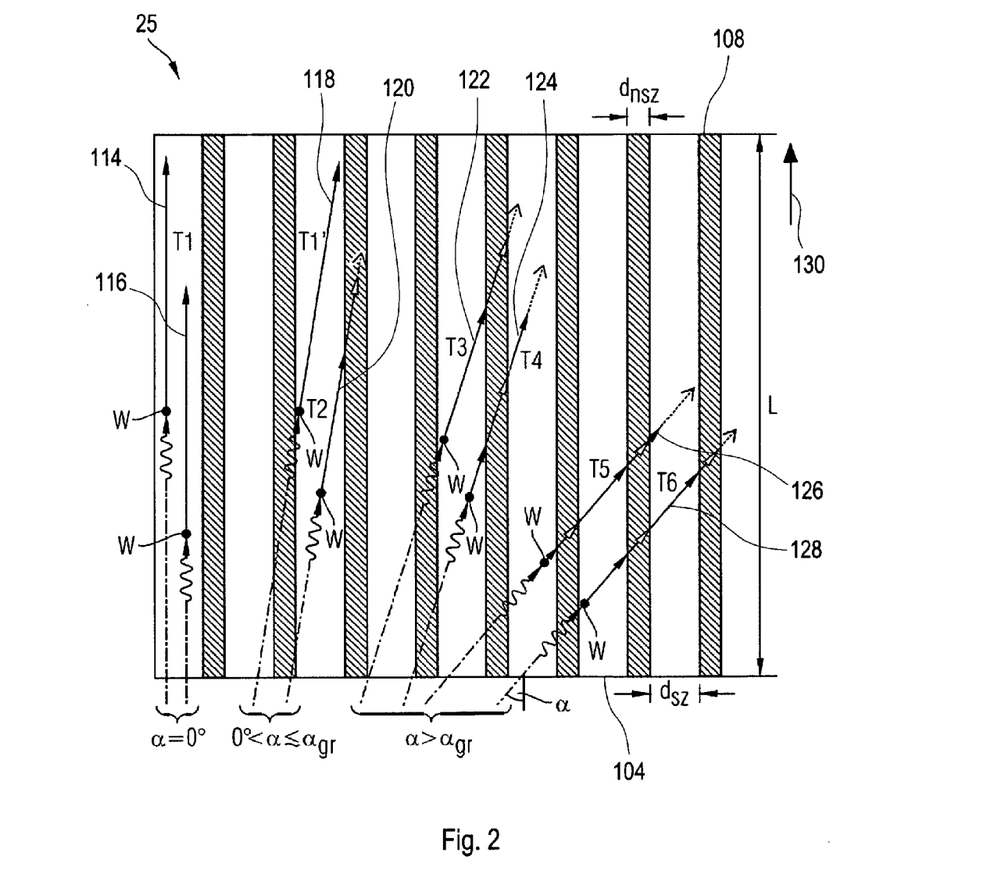
FIG. 2 shows a lamellar second detection means.
Figure 3:
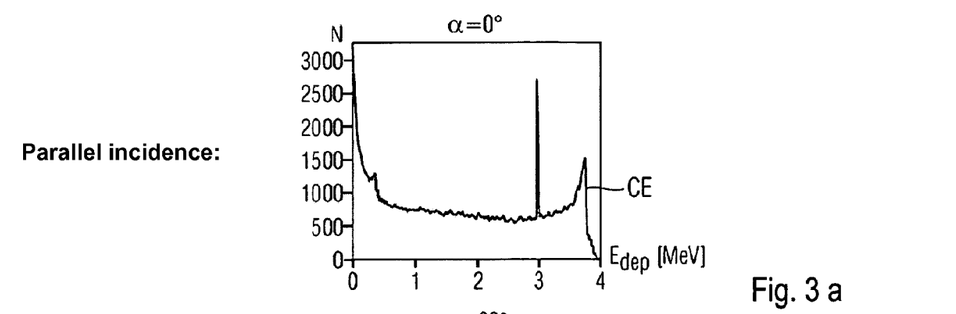
FIGS. 3a, 3b, 3c, 3d show measured diagrams of the second detection means: count rate as a function of energy $E_{dep}$.

FIG. 2 shows the second detection means 25 of FIG. 1 with an arrangement of plates or lamellae 1 to 10 in a longitudinal section. The longitudinal section runs parallel to the face 104 of the second detection means 25. The arrows 114 and 116 show the trajectories of photons and of electrons generated by them, which strike the face 104 perpendicularly and thus "run" parallel to the course of the plates. The electrons can deposit their entire energy into a plate, provided that it is long enough. The arrows 118 and 120 indicate trajectories of photons and of electrons formed by them, which strike the face 104 of the second detection means 25 at an angle $\alpha_1$. Here, the angle $\alpha_1$ is preferably between zero degrees (0°) and an angle $\alpha_{gr}$. Arrows 122 and 128 indicate trajectories which strike the face 104 at an angle $\alpha_2$, said angle $\alpha_2$ being larger than $\alpha_1$. Consequently, electrons that run obliquely to the plate direction indicated by the arrow 130 have less of a chance to emit their energy into only one plate. They will pass through several plates and emit their energy into several plates. Hence, it will be possible to measure an energy signal in several plates, and the energy signal will show less deposited energy. FIG. 3 shows such energy spectra. From these signals, the range of the particle beam 22 in the target volume 23 can be determined, that is to say, the site of origin of the photon in the target volume 23 that generates the appertaining electron. For this purpose, the plates 1 to 10 are read out individually and independently of each other. Spectra indicating this are shown in FIG. 3.

At a typical plate thickness of less than 5 mm of one of the plates 1 to 10, a depth resolution is less than 5 mm. For application in tumor therapy, that is to say, in order to determine clinically relevant ranges of the particle beam 22 in the target volume 23, a resolution of typically 1 mm can be achieved with an appropriate arrangement and plate thickness. For this purpose, preferably a second detection means 25 is arranged to the side of the target volume 23, and another detection means (not shown here) having approximately the same structure is arranged below the patient 24 with the target volume 23. An even smaller resolution can be achieved if several detection means 25, 25', 25", etc. are arranged to the side of and below the target volume 23. As a matter of principle, the detection means 25 can be arranged at any position on a circle around the beam axis 102.

The structure of the detection means 25 is explained in greater detail in WO 2008/009528, especially on pages 23 to 27, and in FIGS. 3, 4 and 5, to which reference is hereby made; said detection means 25 is direction-sensitive.

FIG. 3 shows measured energy spectra of the energy of photons or of electrons being formed that has been deposited into plates 1 to 10 of the detection means 25. The count rate N is plotted as a function of the energy $E_{dep}$ in MeV. Here, the energy is preferably the energy of the electrons that has been deposited into a plate of the detection means. Due to the momentum conservation law, the electrons formed in the plates of the second detection means 25 by means of Compton scattering or photon scattering or pair production from the photons will also be oriented forward, i.e. in the direction of the propagation of the originally formed photons. FIG. 3*a* shows an energy spectrum for the case in which the photons strike the detection means 25 parallel to the arrangement of the plates 1 to 10 of said detection means 25. FIG. 3*b* shows an energy spectrum for an angle α wherein α=30°. It can be seen that the number N of the counted or registered photons or electrons is lower at an energy of 3 MeV. N is about 2000 in comparison to approximately N=2800 in the spectrum of FIG. 3*a*. FIG. 3*c* shows an energy spectrum for the case in which α=60° and the count rate N at an energy of 3 MeV is shown to be less than 2000 events. FIG. 3*d* shows an energy spectrum that was taken for photons or electrons at an angle α=90°. Here, the number N of the registered events with an energy of 3 MeV is even lower. The spectra in FIGS. 3*a*, 3*b*, 3*c*, 3*d* are those of individual plates and are to be understood by way of an example. It can be seen on the basis of these spectra that the photons or electrons that strike each individual plate obliquely can contribute less in the high-energy part (at about 3 MeV) or that fewer events are registered in each individual plate. As a rule, these are plates of the detection means 25 that lie beyond the range of ions in the target volume 23. As a result, the photons cannot strike the face 104 of the plate perpendicularly. Typically, the plates with the numbers 4, 5, 6, 7, 8 are those that the photons can strike perpendicularly to the face 104. The plates with the numbers 9 and 10 as well as 1 to 3 only receive photons at an oblique angle of incidence. These photons, which strike the plates 1 to 3 and 9 to 10, emit less energy into the plate. The reason is that, due to the geometric circumstances, the photons cannot strike the plates 1 to 3 and 9 and 10 of the detection means 25 in parallel.

Figure 4:
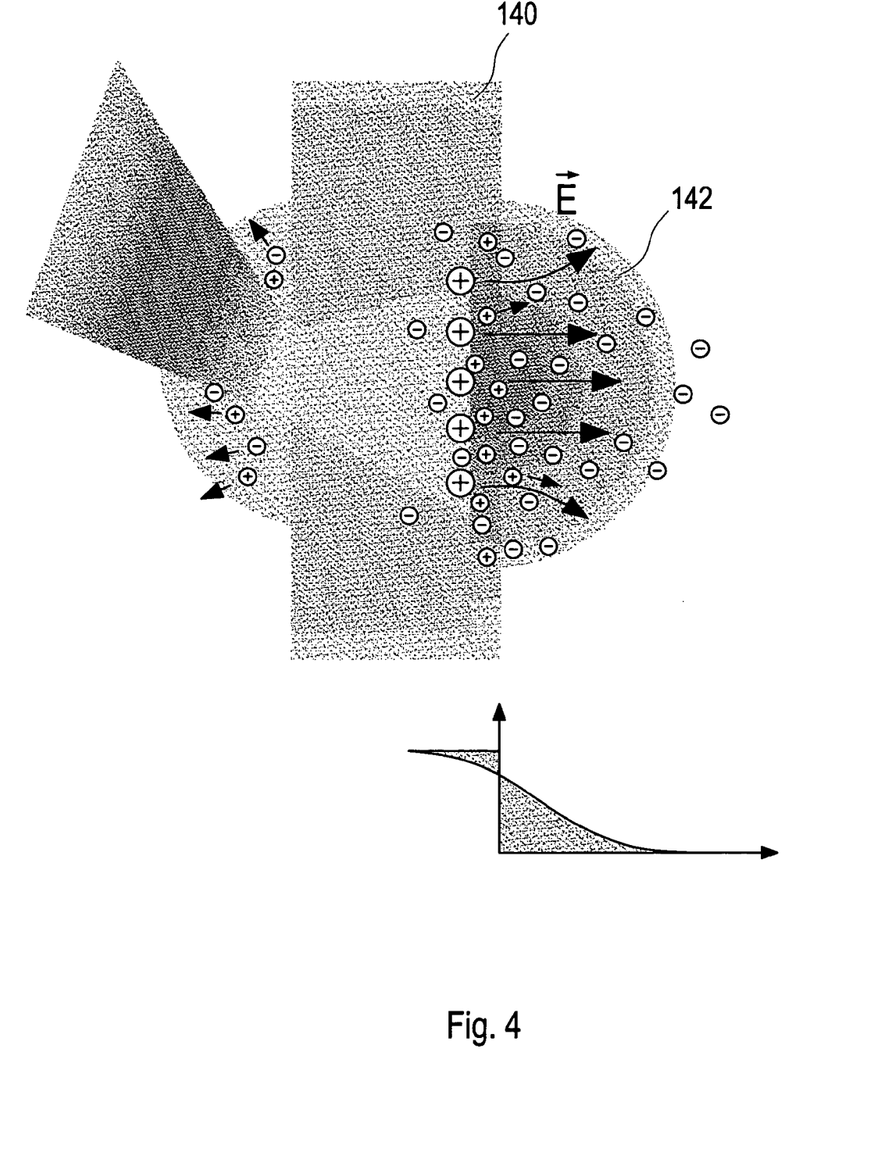
FIG. 4 shows processes when a laser beam passes through a film.

FIG. 4 shows a schematic diagram of the processes that play a role in the technique of a laser-driven accelerator. A short-time pulse laser generates photon pulses with a very high intensity (preferably in the petawatt range) within a time window of femtoseconds and they are fired onto a thin carbon film 140. In the film, first of all, electrons (marked with "−") are released from an atomic union of the carbon film 140, and they form a plasma 142, whereby the remaining ions (marked with "+") can be accelerated to several MeV by field strengths of approximately $10^{12}$ Tesla per meter within very short acceleration distances of less than one millimeter. These accelerated ions can form a particle beam that can be shaped into a particle beam that is designated, for example, in FIGS. 1 and 5, with the reference numeral 22. This particle beam 22 is used to irradiate the target volume 23. This particle beam 22 or ion beam is not shown in FIG. 4.

Figure 5:
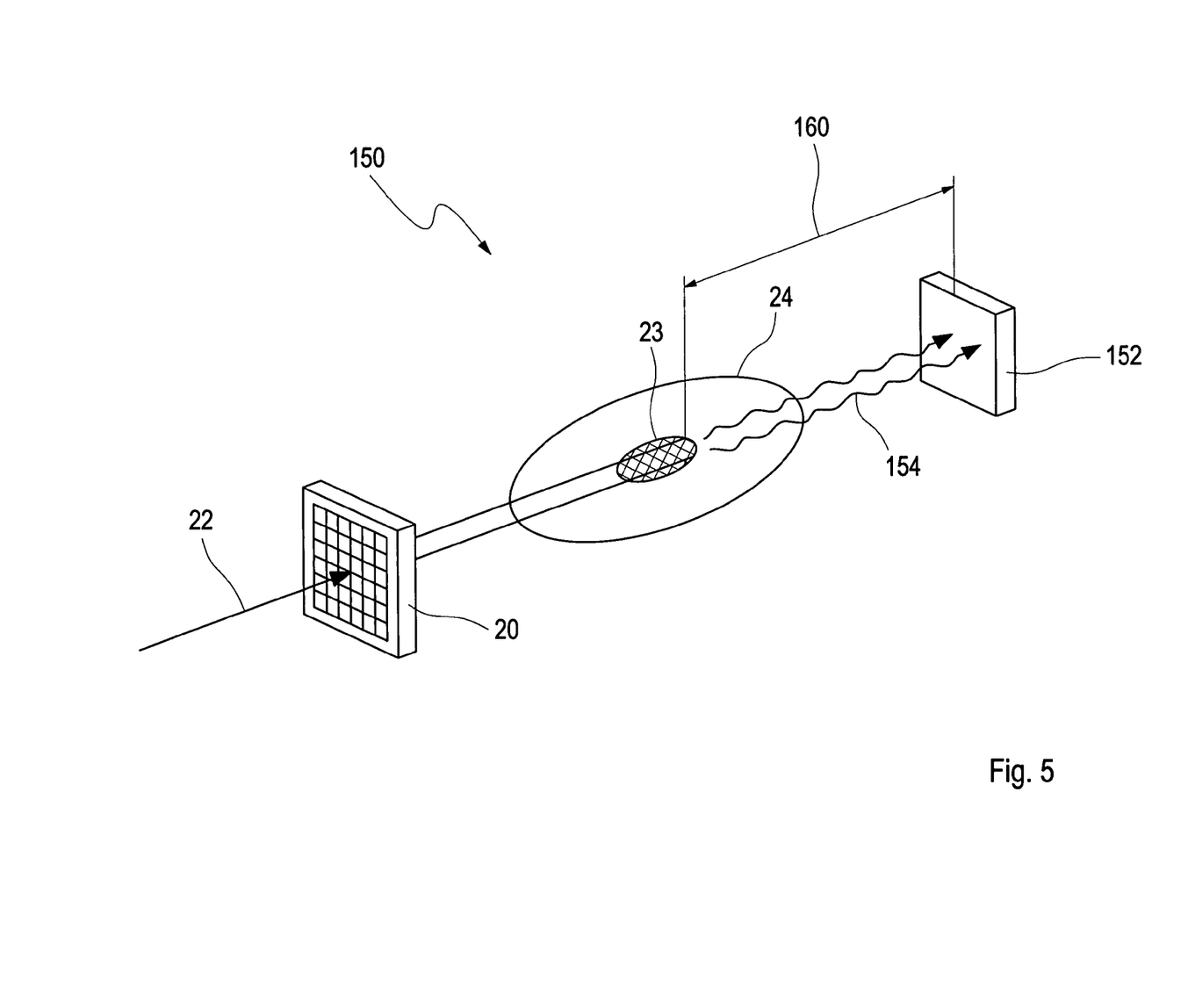
FIG. 5 shows a detector device with an arrangement for measuring the time-of-flight.

FIG. 5 shows a schematic depiction of a detection device 150. The detection device 150 is preferably used with a laser-driven accelerator having very short pulse durations for the ion beam 22. The detection device 150 has a first detection means 20. It can be, for instance, a wire chamber. The detection means 20 can be used to determine the direction of the particle beam or its lateral position in the x- and y-directions. Moreover, the detection device 150 has a second detection means 152. The second detection means 152, as seen in the direction of the particle beam 22, is arranged behind the target volume 23 and serves as a stop detector. The photons, especially gamma quanta, that are generated in the target volume 23 are registered in the second detection means 152. They can be stopped in the second detection means 152, depending on its thickness and material. The second detection means 152 is preferably a generally known plastic detector or a generally known diamond detector, preferably made of polycrystalline diamond. The precise position of the gamma irradiation 154 generated in the target volume 23 can be determined on the basis of the position of the stop detector 152 or of a flight distance 160, which results from the distance between the target volume 23 and the detection means 152, and on the basis of the measured time-of-flight. Thus, the penetration depth of the particle beam 22 applied to the target volume 23 can be determined. In addition to the second detection means 152, additional stop detectors (not shown here) can also be arranged at various angles with respect to the particle beam 22.

The special features of a laser-driven particle accelerator and the relationship to the detection of the penetration depth in the target volume 23 are explained in general terms below. In the case of the laser-driven particle accelerators, the resolution over time of the particle beam depends essentially on the energy resolution of the generated particle pulse and, in the future application of this acceleration technology, this will have reached the requisite value of a few percent. So far, the laser-accelerated accelerators are still in the experimental stage. Realistically, one can assume a resolution over time in the range of a few picoseconds. Thus, it can be determined when the corresponding particle pulse or particle beam 22 is irradiated onto the body or the patient 24.

In the patient 24, at a deceleration distance to the target volume 23, which can be the tumor tissue, the energy scattering and thus the scattering over time of the emitted prompt gamma quanta will only expand by a few percent. Thus, one can assume that the prompt gamma quanta are likewise emitted with a resolution of picoseconds. The distance between the location where the gamma quanta are generated and a prompt gamma detection can be converted into a time-of-flight. The light has a speed of 0.3 mm/picosecond. This means that the distance from the site of origin of the photons can be determined precisely to within a millimeter by measuring the time-of-flight of the emitted gamma quanta in the detection means 52, that is to say, in a counter outside of the body 24.

The detection method can therefore be a TOF method (TOF: time of flight) by means of which the penetration depth of the (particle) beam in the patient 24 can be measured. The formation time of the prompt gamma quanta is—as described above in conjunction with laser-pulsed generation—precisely known within picoseconds. This signal can serve as a starting signal. In a fast detector (second detection means 52, arranged on the beam axis 102) outside of the patient 24, the striking of the gamma quanta is measured and determined on the basis of the time of flight to cover the distance to the second detection means 52, which functions as a stop detector. The measured signal results from all of the gamma quanta produced, irrespective of the energy, since the light speed does not depend on the energy.

In order to measure the penetration depth, the stop detector (second detection means 52) can be arranged in the beam direction on the distal side of the site of origin of the photons. The generally known plastic detectors or else, for example, polycrystalline diamond detectors can be used as stop detectors. The measurement of the time of flight of the synchronously generated photons then yields the precise position of the source/origin of the gamma radiation, that is to say, the location where the ion beams strike the target volume 23, for example, of the patient. By using additional stop detectors at various angles relative to the primary beam (axis of the initial particle beam), suitable programs can then reconstruct the position of each partial beam in the patient 24.

Figure 6:
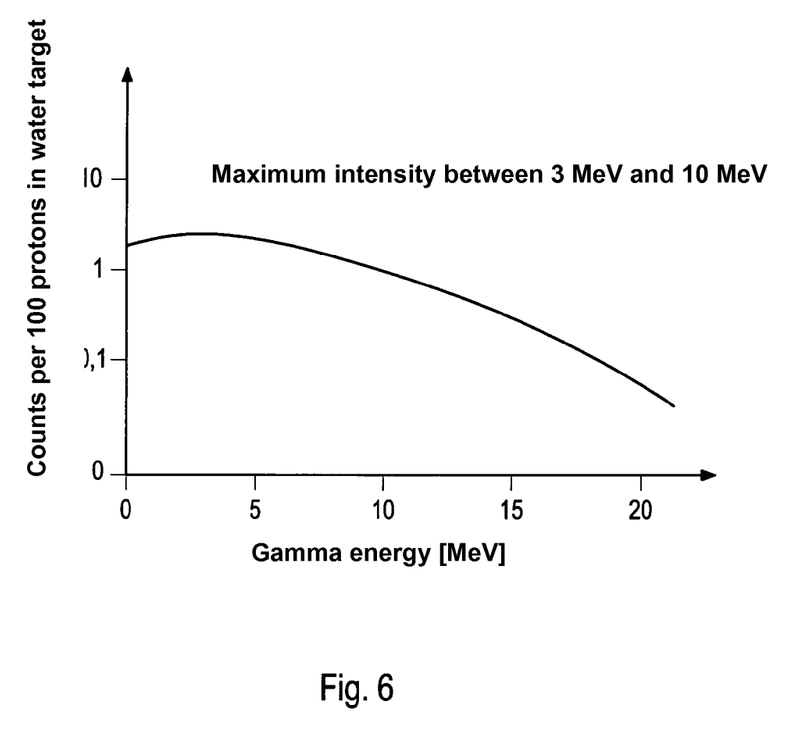
FIG. 6 shows a diagram in which a count rate of photons is plotted as a function of the photon energy.

FIG. 6 depicts a diagram showing that photons are formed when a water target is fired with protons. In the diagram, the number of photons being formed on the y-axis is plotted as a function of their energy on the x-axis. Here, a determination is made of the number of the photons being formed per one hundred protons fired at a water target. The intensity of the photons being formed is essentially between 3 MeV and 10 MeV. This corresponds approximately to the number and to the energy of the photons that would be formed if a particle beam of protons were fired at a human tissue. Thus, the diagram shows that, when particle beams are deposited in human tissue, photons with an energy of approximately 3 MeV to 10 MeV are formed. These photons are also referred to as gamma quanta, and thus have a continuous energy spectrum of up to several MeV and they are emitted isotropically around the particle beam deposited in the target volume. During the deceleration process of the ions in the patient, such high-energy gamma quanta with energies of up to several MeV are formed. These quanta essentially leave the patient and can be detected from the outside. The number depends on the number of deposited particles. The photons that are to be detected by the second detection means 25 and 52 can thus determine this energy distribution. Consequently, a detection means 25 and/or 52 is set up in such a way that they can detect photons in the energy range between about 3 MeV and 10 MeV. Thus, the detection of these so-called prompt gamma quanta, that is to say, electromagnetic radiation that is emitted during the deceleration process, can serve to detect the location where the particles of the particle beam 22 are deposited in the target volume 23. Consequently, due to a combination of the first detection means 20 and of the second detection means 25, a direction-resolved detection is achieved with which the source of the gamma rays can be located. The measurement of the prompt gamma quanta makes it possible to determine the penetration depth of the particle beam 22 in the target volume 23.

Here, the detector device is structured differently, depending on the particle beam. In the case of a continuous beam of the type found in a synchrotron or cyclotron with an acceleration means, a combination of the spatially resolving particle detector (detection means 20) can be used for the particle beam 22 in front of the patient 24 with the laminated range gamma detector (second detection means 25), which is installed next to the patient parallel to the therapeutic beam. A detector element known from the prior art can be used for this purpose. In a spatially resolving particle transmission detector (such as, for example, wire chambers, pixel ionization chambers or other spatially resolving transmission counters with a low area density), the lateral (x-y) coordinates are specified for the particle beam of each voxel element. Consequently, due to the defined beam control in front of the patient or body, the beam direction in the patient or body is also defined.

As already explained in the description relating to FIGS. 1 and 2, the measurement of the penetration depth was carried out with the laminated gamma detector, known from the prior art, as detector device 25. In this context, this depth can be determined without the use of a collimator and thus with high efficiency: in the case of high-energy photons/gamma quanta, due to the momentum conservation law, the secondary products, that is to say, the Compton or photo or pair production electrons, are scattered forward, i.e. in the direction of the propagation of the original photon. Since the detection means consists of or is structured with individual, especially thin lamellae, i.e. plates, the only electrons that have a chance to deposit all of their energy into the detection means 25 are those that have entered parallel to the orientation of the plate (see FIG. 2). As is known from the prior art, electrons that strike obliquely will have less of a chance to deposit their energy into one plate.

Similar to the detection system known from the prior art, these types of detectors are direction-sensitive. In contrast to the land mine detectors of WO 2008/009528, for example, in which the direction of a source is located, the detection means 25 can be used to measure a range. For this reason, the detector material ranges (plates made of detector material) could be read out individually, that is to say, independently of each other. Detectors that are beyond the range of the ions in the patient are only reached by gamma quanta that can no longer strike in parallel and that therefore contribute little in the high-energy part of the energy spectrum.

The direct detection of photons that are formed in the target volume offers advantages over other methods, which will be explained below: if the intention is to achieve irradiation that conforms most closely to the target, an active adaptation is carried out, the so-called intensity-modulated particle therapy (IMPT), in which the target volume is broken down into 20,000 to 50,000 small individual volumes (voxels) that are then irradiated one after the other within a few minutes. For the IMPT, a simultaneous measurement of the positron decay of the isotopes $^{10}$C and $^{11}$C produced in the patient, the so-called in-beam PET, was developed as a quality assurance and employed in the Darmstadt heavy-ion therapy. With this technique, it was possible to determine the range distribution of the beam in the patient after each irradiation fraction, and discrepancies were recognized and corrected in a small percentage of the patients. However, the analysis by means of PET can only be carried out after the irradiation since the two essential PET isotopes $^{10}$C and $^{11}$C have lifetimes of 19 seconds and 20 seconds, respectively.

A similar analysis for a quality assurance of the dose deposition in the patient was also proposed and tested for proton therapy, in which primarily the positron emitter $^{15}$O was analyzed (half-life: 2 minutes). Therefore, a drawback of the known methods is the fact that even though this PET analysis is possible with other ion projectiles, due to the individual half-lives, it can only be carried out on the basis of a posthumous analysis after each fraction.

Consequently, no simultaneous observation of the beam in the patient can be achieved. At the present time, aside from the in-beam PET of the type used by the GSI Helmholtz Centre for Heavy Ion Research GmbH, no standard method exists that could be used clinically for the analysis of the prompt gamma quanta, that is to say, for finding the location of the beam in the patient.

The energy-resolving spectrometers that are normally used in physics are unsuitable for this since for one thing, they provide the wrong information: energy instead of location, and since they also have a lower efficiency (response probability only in the range of a few percent), and since this efficiency generally decreases with the gamma energy and is low for the MeV range.

Scintillation gamma detectors such as NaJ or plastic scintillators or other gamma detectors (Si or Ge semiconductors) do not themselves have any directional resolution. This could be achieved by an upstream collimator, but once again, this would come at the expense of the efficiency. It is not possible to effectively use collimator-free Compton detector arrangements in which, in a first scatter film, the photon is made to emit an electron out of the film and then, from the analysis of the total kinetics, the site of origin or the direction of the primary photon/gamma quantum is determined. This is because Compton counters also have a low efficiency of just a few percent and are thus hardly suitable for clinical use.

This is why the detector device according to embodiments of the invention and the method, which measure the prompt emitted gamma quanta, are advantageous. Here, the gamma quanta have a different time structure, depending on the time structure of the therapy beam, i.e. depending on whether the ion beam is emitted continuously (or quasi continuously) as is the case with a synchrotron, or whether the beam is emitted in micropulses like with the laser-driven accelerators that are currently being developed. (The cyclotron with its time structure is more similar to the pulsed types of accelerators.)

Figure 7:
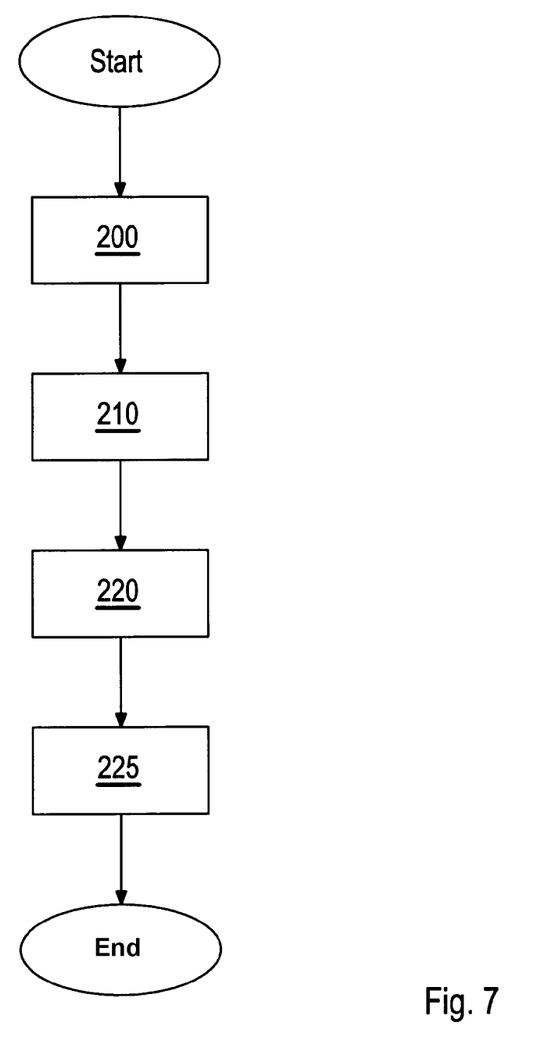
FIG. 7 shows a flow chart of a method according to an embodiment of the invention.

FIG. 7 shows a method with which the penetration depth of a particle beam 22 in a target volume 23 of an object 24 that is to be irradiated can be determined. The direction of the particle beam is determined in method step 200. This can preferably be done with a first detection means 20 that determines at least one lateral position of the particle beam 22. The z-position of photons that are formed by the particle beam 22 in the target volume 23 is determined with a spatially-resolving detection means in a second method step 210. In method step 210, the determined x- or y-position of the particle beam 22 in the target volume 23 and the determined z-position are combined, and an irradiated matrix dot in the target volume is determined. A control signal can be emitted in method step 225. The control signal can be fed into one control unit in order to control the radiation device and/or the acceleration means.

In one embodiment of the method, as an alternative, the method step 210 can be carried out by measuring the time-of-flight of the photons that are emitted forward, that is to say, as seen in the beam direction. The distance between the second detection means that serves as a stop detector for the photons and the site of origin of the photons in the target volume due to the particle beam is determined by means of the measurement of the time-of-flight of the photons. In this manner, the precise site of origin of the photons in the target volume can be determined. Here, the second detection means 52 is positioned at essentially zero degrees, preferably on the beam axis 102. Thus, the penetration depth of the particle beam 22 in the target volume 23 can be determined.

While the invention has been particularly shown and described with reference to preferred embodiments thereof, it will be understood by those skilled in the art that various changes in form and details may be made therein without departing from the spirit and scope of the invention.

What is claimed is:

1. A detector device for detecting a penetration depth of a particle beam applied to a target volume, the detector device comprising:
   a first detection device; and
   a second detection device configured to detect photons that are formed in the target volume, the second detection device being disposed behind the first detection device with respect to a direction of the particle beam.

2. The detector device recited in claim 1, wherein the second detection device is configured to detect gamma quanta.

3. The detector device recited in claim 1, wherein the first detection device is configured to determine a direction of the particle beam in at least a first lateral dimension.

4. The detector device recited in claim 3, wherein the first detection device is configured to determine a direction of the particle beam in a second lateral dimension, the second lateral dimension differing from the first lateral dimension.

5. The detector device recited in claim 1, wherein the first detection device is one of an ionization chamber and a wire chamber.

6. The detector device recited in claim 1, wherein the second detection device is configured to spatially resolve the detected photons that are formed in the target volume.

7. The detector device recited in claim 1, wherein the second detection device includes a lamellar structure.

8. The detector device recited in claim 7, wherein lamellae of the second detection device are disposed so as to have a face oriented perpendicular to an axis of the particle beam.

9. The detector device recited in claim 1 wherein the second detection device includes a stop detector configured to determine an origin of a detected photon based on a distance between the target volume and the second detection device and a measured time-of-flight of the photon.

10. A radiation device for irradiating a target volume in an object, the radiation device comprising:
    an acceleration device and a controller for controlling a particle beam; and
    a detector device including:
       a first detection device; and
       a second detection device configured to detect photons that are formed in the target volume, the second detection device being disposed behind the first detection device with respect to a direction of the particle beam.

11. The radiation device recited in claim 10, wherein the detector device is configured to generate a control signal, the controller being configured to receive the control signal.

12. The radiation device recited in claim 10, wherein the first detection device and the second detection device are disposed in two different positions relative to the target volume.

13. The radiation device recited in claim 12, wherein the two different positions are perpendicular to each other.

14. A method for determining a penetration depth of a particle beam into an object, the method comprising:
    providing a detector device including:
       a first detection device; and
       a second detection device configured to detect photons that are formed in the object, the second detection device being disposed behind the first detection device with respect to a direction of the particle beam;
    irradiating the object with the particle beam so as to form the photons by an interaction of the particle beam with the object; and
    detecting the photons using the detector device.

15. The method recited in claim 14, wherein the particle beam is irradiated into a target volume of the object so as to form the photons in the target volume.

16. The method recited in claim 14, wherein a direction of the particle beam is detected using the detector device.

17. The method recited in claim 16, wherein the detecting the direction includes detecting a lateral location of the particle beam in a target volume of the object.

18. The method recited in claim 16, wherein the detecting a direction is performed using a spatially resolved detection device.

19. The method recited in claim 14, wherein the detecting the photons includes detecting photons at positions outside of an axis of the particle beam.

20. The method recited in claim 14, wherein a site of origin of the photons in a target volume of the object is determined by measuring a time-of-flight of the photons from the site of origin in the target volume to the second detection device.

* * * * *